(12) United States Patent
Rahim et al.

(10) Patent No.: US 9,348,013 B2
(45) Date of Patent: May 24, 2016

(54) ITEM HANGER ARRANGEMENT, SYSTEM, AND METHOD

(71) Applicant: Mobile Aspects, Inc., Pittsburgh, PA (US)

(72) Inventors: Muhammad R. Rahim, Monroeville, PA (US); Pribadi Kardono, Monroeville, PA (US); Khang Nguyen Le, Murrieta, CA (US); Timur P. Sriharto, Monroeville, PA (US)

(73) Assignee: Mobile Aspects, Inc., Pittsburgh, PA (US)

( * ) Notice: Subject to any disclaimer, the term of this patent is extended or adjusted under 35 U.S.C. 154(b) by 16 days.

(21) Appl. No.: 14/487,809

(22) Filed: Sep. 16, 2014

(65) Prior Publication Data
US 2015/0077249 A1  Mar. 19, 2015

Related U.S. Application Data

(60) Provisional application No. 61/879,381, filed on Sep. 18, 2013.

(51) Int. Cl.

| | | |
|---|---|---|
| *G08B 21/00* | (2006.01) | |
| *G01S 5/02* | (2010.01) | |
| *G08B 13/14* | (2006.01) | |
| *A61B 1/00* | (2006.01) | |
| *G06Q 10/08* | (2012.01) | |
| *G06K 17/00* | (2006.01) | |

(52) U.S. Cl.
CPC ............ *G01S 5/0294* (2013.01); *A61B 1/00131* (2013.01); *A61B 1/00147* (2013.01); *G08B 13/1427* (2013.01); *G06K 2017/0045* (2013.01); *G06Q 10/087* (2013.01)

(58) Field of Classification Search
CPC ................ G06K 2017/0045; G06Q 10/087
See application file for complete search history.

(56) References Cited

U.S. PATENT DOCUMENTS

| | | | |
|---|---|---|---|
| 3,958,102 | A | 5/1976 | Burt |
| 4,116,512 | A | 9/1978 | Wiser |
| 4,118,693 | A | 10/1978 | Novikoff |

(Continued)

FOREIGN PATENT DOCUMENTS

| | | | |
|---|---|---|---|
| JP | 2001052054 A | 2/2001 | |
| JP | 2002282200 A | 10/2002 | |

OTHER PUBLICATIONS

U.S. Appl. No. 14/013,625, filed Aug. 29, 2013.
U.S. Appl. No. 14/524,542, filed Sep. 27, 2014.
U.S. Appl. No. 14/455,131, filed Aug. 8, 2014.
U.S. Appl. No. 14/558,064, filed Dec. 2, 2014.
U.S. Appl. No. 13/662,897, filed Oct. 29, 2012.
U.S. Appl. No. 13/793,201, filed Mar. 11, 2013.

*Primary Examiner* — Shirley Lu
(74) *Attorney, Agent, or Firm* — The Webb Law Firm (57) ABSTRACT

A system for supporting and tracking at least one item includes a plurality of support structures adapted to support at least one item, at least one signal receiving arrangement associated with the plurality of support structures, at least one indicator arrangement associated with the plurality of support structures, and at least one controller in communication with the at least one signal receiving arrangement and the at least one indicator arrangement. The at least one signal receiving arrangement is configured to receive data from a transponder associated with the at least one item. The controller is programmed and/or configured to control the plurality of indicator arrangements based at least partially on at least a portion of the data received from the at least one signal receiving arrangement.

10 Claims, 10 Drawing Sheets

(56) References Cited

U.S. PATENT DOCUMENTS

| | | | |
|---|---|---|---|
| 4,227,037 A | 10/1980 | Layton | |
| 4,496,406 A | 1/1985 | Dedow | |
| 4,636,634 A | 1/1987 | Harper et al. | |
| 4,636,950 A | 1/1987 | Caswell et al. | |
| 4,673,932 A | 6/1987 | Ekchian et al. | |
| 4,847,764 A | 7/1989 | Halvorson | |
| 4,860,918 A | 8/1989 | Wuyten et al. | |
| 5,029,183 A | 7/1991 | Tymes | |
| 5,194,856 A | 3/1993 | Zijlstra | |
| 5,287,414 A | 2/1994 | Foster | |
| 5,295,154 A | 3/1994 | Meier et al. | |
| 5,389,919 A | 2/1995 | Warren et al. | |
| 5,408,443 A | 4/1995 | Weinberger | |
| 5,410,315 A | 4/1995 | Huber | |
| 5,413,236 A | 5/1995 | Kenevan | |
| 5,431,299 A | 7/1995 | Brewer et al. | |
| 5,495,961 A | 3/1996 | Maestre | |
| 5,565,858 A | 10/1996 | Guthrie | |
| 5,689,238 A | 11/1997 | Cannon, Jr. et al. | |
| 5,713,485 A | 2/1998 | Liff et al. | |
| 5,729,697 A | 3/1998 | Schkolnick et al. | |
| 5,739,765 A | 4/1998 | Stanfield et al. | |
| 5,751,220 A | 5/1998 | Ghaffari | |
| 5,751,221 A | 5/1998 | Stanfield et al. | |
| 5,765,707 A | 6/1998 | Kenevan | |
| 5,771,003 A | 6/1998 | Seymour | |
| 5,774,053 A | 6/1998 | Porter | |
| 5,774,059 A | 6/1998 | Henry et al. | |
| 5,797,515 A | 8/1998 | Liff et al. | |
| 5,801,628 A | 9/1998 | Maloney | |
| 5,804,810 A | 9/1998 | Woolley et al. | |
| 5,857,152 A | 1/1999 | Everett | |
| 5,912,818 A | 6/1999 | McGrady et al. | |
| 5,917,433 A | 6/1999 | Keillor et al. | |
| 5,936,527 A | 8/1999 | Isaacman et al. | |
| 5,950,630 A | 9/1999 | Portwood et al. | |
| 5,993,046 A | 11/1999 | McGrady et al. | |
| 6,075,441 A | 6/2000 | Maloney | |
| 6,112,502 A | 9/2000 | Frederick et al. | |
| 6,116,461 A | 9/2000 | Broadfield et al. | |
| 6,127,928 A | 10/2000 | Issacman et al. | |
| 6,204,764 B1 | 3/2001 | Maloney | |
| 6,296,148 B1 | 10/2001 | Myers et al. | |
| 6,323,782 B1 | 11/2001 | Stephens et al. | |
| 6,392,544 B1 | 5/2002 | Collins | |
| 6,407,665 B2 | 6/2002 | Maloney | |
| 6,424,262 B2 | 7/2002 | Garber et al. | |
| 6,445,297 B1 | 9/2002 | Nicholson | |
| 6,512,459 B2 | 1/2003 | Benezech et al. | |
| 6,512,478 B1 | 1/2003 | Chien | |
| 6,677,857 B2 | 1/2004 | Bara et al. | |
| 6,703,935 B1 | 3/2004 | Chung et al. | |
| 6,707,381 B1 | 3/2004 | Maloney | |
| 6,714,121 B1 | 3/2004 | Moore | |
| 6,718,888 B2 | 4/2004 | Muirhead | |
| 6,745,027 B2 | 6/2004 | Twitchell, Jr. | |
| 6,747,558 B1 | 6/2004 | Thorne et al. | |
| 6,750,771 B1 | 6/2004 | Brand | |
| 6,762,676 B2 | 7/2004 | Teowee et al. | |
| 6,826,514 B1 | 11/2004 | Antico et al. | |
| 6,870,464 B2 | 3/2005 | Okamura | |
| 6,943,678 B2 | 9/2005 | Muirhead | |
| 6,989,749 B2 | 1/2006 | Mohr | |
| 7,009,518 B2 | 3/2006 | Liao et al. | |
| 7,009,576 B2 | 3/2006 | Adamson et al. | |
| 7,126,926 B1 | 10/2006 | Bjorklund et al. | |
| 7,130,773 B1 | 10/2006 | Wong | |
| 7,135,973 B2 | 11/2006 | Kittel et al. | |
| 7,152,791 B2 | 12/2006 | Chappidi et al. | |
| 7,187,287 B2 | 3/2007 | Ryal | |
| 7,233,620 B2 | 6/2007 | Brommer | |
| 7,256,682 B2 | 8/2007 | Sweeney, II | |
| 7,265,675 B1 | 9/2007 | Carrender et al. | |
| 7,286,043 B2 | 10/2007 | Carrender et al. | |
| 7,298,243 B2 | 11/2007 | Juels et al. | |
| 7,310,045 B2 | 12/2007 | Inui | |
| 7,318,261 B2 | 1/2008 | Bills | |
| 7,342,496 B2 | 3/2008 | Muirhead | |
| 7,348,884 B2 | 3/2008 | Higham | |
| 7,401,375 B2 | 7/2008 | McLeod | |
| 7,420,458 B1 | 9/2008 | Kuzma et al. | |
| 7,433,648 B2 | 10/2008 | Bridgelall | |
| 7,758,523 B2 | 7/2010 | Collings et al. | |
| 8,072,333 B2 * | 12/2011 | Ferguson | G06K 19/07745 235/492 |
| 8,120,497 B2 | 2/2012 | Binmore | |
| 8,484,049 B2 | 7/2013 | Mullenger et al. | |
| 2001/0002448 A1 | 5/2001 | Wilson et al. | |
| 2001/0028308 A1 | 10/2001 | De La Huerga | |
| 2001/0034613 A1 | 10/2001 | Rubsamen | |
| 2001/0044731 A1 | 11/2001 | Coffman et al. | |
| 2001/0052054 A1 | 12/2001 | Franke et al. | |
| 2002/0027507 A1 | 3/2002 | Yarin et al. | |
| 2002/0038167 A1 | 3/2002 | Chirnomas | |
| 2002/0063622 A1 | 5/2002 | Armstrong et al. | |
| 2002/0113082 A1 | 8/2002 | Leatherman et al. | |
| 2002/0143320 A1 | 10/2002 | Levin | |
| 2002/0145520 A1 | 10/2002 | Maloney | |
| 2002/0153411 A1 | 10/2002 | Wan et al. | |
| 2002/0183882 A1 | 12/2002 | Dearing et al. | |
| 2002/0190871 A1 | 12/2002 | Stanfield et al. | |
| 2003/0030539 A1 | 2/2003 | McGarry et al. | |
| 2003/0034390 A1 | 2/2003 | Linton et al. | |
| 2003/0117281 A1 | 6/2003 | Sriharto | |
| 2003/0160698 A1 | 8/2003 | Andreasson et al. | |
| 2003/0164401 A1 | 9/2003 | Andreasson et al. | |
| 2003/0174099 A1 * | 9/2003 | Bauer | G06K 7/0008 343/893 |
| 2004/0046020 A1 | 3/2004 | Andreasson et al. | |
| 2004/0069850 A1 | 4/2004 | De Wilde | |
| 2004/0069852 A1 | 4/2004 | Seppinen et al. | |
| 2004/0111335 A1 | 6/2004 | Black et al. | |
| 2004/0155003 A1 | 8/2004 | Anderson et al. | |
| 2004/0168618 A1 | 9/2004 | Muirhead | |
| 2004/0267545 A1 | 12/2004 | Buchmann et al. | |
| 2005/0024211 A1 | 2/2005 | Maloney | |
| 2005/0088284 A1 | 4/2005 | Zai et al. | |
| 2005/0088305 A1 | 4/2005 | Greene et al. | |
| 2005/0093679 A1 | 5/2005 | Zai et al. | |
| 2005/0099283 A1 | 5/2005 | Johnson et al. | |
| 2005/0237184 A1 | 10/2005 | Muirhead | |
| 2005/0241548 A1 | 11/2005 | Muirhead | |
| 2005/0280539 A1 | 12/2005 | Pettus | |
| 2006/0022800 A1 | 2/2006 | Krishna et al. | |
| 2006/0028081 A1 | 2/2006 | Minagawa | |
| 2006/0056370 A1 | 3/2006 | Hancock et al. | |
| 2006/0058018 A1 | 3/2006 | Toulis et al. | |
| 2006/0092040 A1 | 5/2006 | Fishkin et al. | |
| 2006/0109084 A1 | 5/2006 | Yarvis | |
| 2006/0143439 A1 | 6/2006 | Arumugam et al. | |
| 2006/0187043 A1 | 8/2006 | Allen | |
| 2006/0215593 A1 | 9/2006 | Wang et al. | |
| 2007/0046467 A1 | 3/2007 | Chakraborty et al. | |
| 2007/0096876 A1 | 5/2007 | Bridgelall et al. | |
| 2007/0103303 A1 | 5/2007 | Shoarinejad | |
| 2007/0164109 A1 | 7/2007 | Ridings et al. | |
| 2007/0171992 A1 | 7/2007 | Shameli et al. | |
| 2007/0172007 A1 | 7/2007 | Shoarinejad et al. | |
| 2007/0188342 A1 | 8/2007 | Valeriano et al. | |
| 2007/0200724 A1 | 8/2007 | Lazo et al. | |
| 2007/0216534 A1 | 9/2007 | Ferguson et al. | |
| 2007/0279202 A1 | 12/2007 | Lionetti | |
| 2008/0061940 A1 | 3/2008 | Onderko et al. | |
| 2008/0117050 A1 | 5/2008 | Wu et al. | |
| 2008/0198016 A1 | 8/2008 | Lawrence et al. | |
| 2008/0218354 A1 | 9/2008 | Lorentz et al. | |
| 2009/0009332 A1 | 1/2009 | Nunez et al. | |
| 2009/0261956 A1 | 10/2009 | Ojeda et al. | |

* cited by examiner

ITEM HANGER ARRANGEMENT, SYSTEM, AND METHOD

CROSS REFERENCE TO RELATED APPLICATIONS

This application claims the benefit of priority from U.S. Provisional Patent Application No. 61/879,381, filed Sep. 18, 2013, which is incorporated by reference in its entirety.

BACKGROUND OF THE INVENTION

1. Field of the Invention

The present invention relates generally to item hanger arrangements and inventory management methods and systems. In particular, the present invention relates to an item hanger arrangement and system, and an indication and tracking system and method for controlling and managing the storage and use of items.

2. Description of Related Art

Presently, in the health care industry, complex and expensive equipment and systems are utilized in the diagnosis and care process. As the development of this equipment and associated systems continues, the necessity to monitor and track the usage is of the utmost importance. Certain drawbacks and deficiencies exist in the prior art, including, (1) theft of the equipment or its components; (2) inaccurate manual compliance and tracking methods; (3) ineffective and inefficient compliance monitoring and similar management; (4) inefficient equipment sharing and distribution; (5) high repair costs; (6) difficulty in tracking; (7) inaccurate identification and tracking methods; and (8) problems identifying specific items from a plurality of items, etc.

Many medical devices, such as endoscopes, are highly complex and expensive medical instruments to purchase, maintain and repair. Unfortunately, equipment theft does occur, with some hospitals reporting the loss of 5-7 endoscopes; which, as stated, are extremely expensive to replace. According to the prior art, and especially in those procedures involving the use of an endoscope or other expensive medical devices, compliance with hospital protocol is a manual process, i.e., using "pen and paper." Such theft and compliance issues arise with a number of expensive medical devices and equipment.

Further, many medical devices are currently being stored in unlocked cabinets, which are often left open, and in some cases, positioned in the middle of a high-traffic hallway. This represents a contamination issue, a potential damage issue, a potential theft/loss issue, a tracking issue, and the like. According to the prior art, and with respect to endoscopes, these devices are routinely returned from procedure rooms if not used during the procedure, and simply re-hung in the cabinet. However, there exists no effective control in place to prevent "dirty" endoscopes from potentially cross-contaminating the entire cabinet.

In addition, compliance monitoring, decontamination (cleaning), and disinfection protocols are manual processes, and time-based measures of workforce efficiencies are virtually nonexistent. Many medical devices, even when not in use, may require regularly scheduled cleaning and/or disinfecting due to an accumulation of dust and other contaminates. Another issue arises when such devices are borrowed by other departments, and are subsequently lost or misplaced. Accordingly, the devices are not available when required by the appropriate personnel. In addition, the hospitals must then assign individuals to spend time locating these expensive instruments. Since the sign-out procedures are normally manual, users may forget to sign out the equipment according to the procedure.

The repair costs associated with an endoscope, among other medical devices, is very high, and on some occasions, individual endoscopes can be "lemons" and require additional repair (with the associated costs). Some doctors report damage often, which will trigger excessive repair costs. Presently, there is no effective way of determining if a specific individual is the common factor in multiple damaged endoscopes. Still further, there is no effective process to identify and track loaner scopes, and little data is available to the managers of any "Continuous Improvement" process, i.e., there is no way of knowing if an endoscope has been lost. Presently, recordkeeping directed to these endoscopes is manual and time-intensive.

Preventive maintenance of various medical devices is often ad-hoc at times, and existing systems are often not integrated into the process to manage and tune preventative maintenance cycles and activities. Additionally, while many devices do have individual and unique serial numbers, trying to locate this number amongst a tangled jumble of insertion tubes and umbilical cables is extremely difficult, and since endoscope pools are not load-rotated, the scopes in front get used more often, etc.

Accordingly, such prior art storage, tracking, and inventory management systems are ineffective and/or inefficient in monitoring, tracking and communicating information directed to specified equipment and devices, e.g., an endoscope or the like.

SUMMARY OF THE INVENTION

Generally, provided is an improved item hanger arrangement and system, and an improved indication and tracking system for managing the storage and use of items, such as medical devices and items, e.g., endoscopes and/or the like.

According to one preferred and non-limiting embodiment, provided is a system for supporting and tracking at least one item. The system includes a plurality of support structures, each support structure adapted to support at least one item; at least one signal receiving arrangement associated with the plurality of support structures, wherein the at least one signal receiving arrangement is configured to receive data from a transponder associated with the at least one item; at least one indicator arrangement associated with the plurality of support structures; and at least one controller in communication with the at least one signal receiving arrangement and the at least one indicator arrangement, the at least one controller programmed and/or configured to control the plurality of indicator arrangements based at least partially on at least a portion of the data received from the at least one signal receiving arrangement.

In non-limiting embodiments, the system may further include a plurality of transponders, wherein each transponder of the plurality of transponders is adapted to be fixed on an item. In some examples, each transponder may include at least a portion of the data received by the at least one signal receiving arrangement, and the data may include an identifier that uniquely identifies the at least one item (or the type or category of item) in at least one data structure.

In some non-limiting embodiments, each support structure may include at least two upright members, and at least one upright member of each support structure may include at least a portion of the at least one signal receiving arrangement. For example, the at least one signal receiving arrangement may include at least a first antenna and a second antenna, wherein a first upright member of the first antenna includes a positive portion of the first antenna, wherein a second upright member of the first antenna includes a negative portion of the first antenna, wherein a first upright member of the second antenna includes a negative portion of the second antenna, wherein a second upright member of the second antenna includes a positive portion of the second antenna, and wherein the first antenna and second antenna are arranged such that the first upright member of the first antenna and the first upright member of the second antenna are substantially substantially adjacent.

In non-limiting embodiments, the at least one indicator arrangement may include a plurality of indicator arrangements, wherein each indicator arrangement of the plurality of indicator arrangements corresponds to a support structure of the plurality of support structures, and wherein the at least one controller is further programmed and/or configured to cause each indication arrangement to indicate at least one state or condition of at least one item supported by the corresponding support structure. In some non-limiting embodiments, the at least one state indicates at least one of the following: an alarm, a condition, a location, or any combination thereof. Moreover, each indicator arrangement may be substantially adjacent its corresponding support structure in some non-limiting embodiments. As an example, and in non-limiting embodiments, the at least one controller may be further programmed and/or configured to cause the at least one indicator arrangement to indicate at least one state of at least one item supported by the corresponding support structure, wherein the at least one item is a medical device, and wherein the at least one state includes at least one of the following: an indication that the medical device is clean, an indication that the medical device requires cleaning, an indication that the medical device has been removed from the support structure, an indication that the medical device has been removed from a facility or location, an indication that the medical device requires repair, or any combination thereof.

In non-limiting embodiments, the system may further include a plurality of transponders, each transponder adapted to be placed substantially adjacent an end portion of an endoscope. The system, in non-limiting embodiments, may also include at least one locking device configured to releasably lock an item to at least one of the plurality of support structures, wherein the at least one controller is programmed and/or configured to operate the at least one locking device based at least partially on user authentication. Further, the at least one indicator arrangement may include at least one display device that displays a graphical user interface, the graphical user interface including at least one visual indication of at least one state of at least one item. Further non-limiting embodiments of the system may include a container having an interior, the interior of the container including the plurality of support structures, wherein the container has at least one door, and wherein the controller is configured to read the data with the signal receiving arrangement for each support structure based on a state or movement of the at least one door.

According to another preferred and non-limiting embodiment, provided is a system for hanging a plurality of items, including: a plurality of support structures adapted to hang a plurality of items, each support structure including an antenna at least partially integral with the support structure; and at least one controller in communication with the antenna of each support structure, the at least one controller programmed and/or configured to receive data from the plurality of items on the plurality of support structures via the antenna.

In non-limiting embodiments, the system may further include at least one indicator in communication with the at least one controller, wherein the controller is further programmed and/or configured to control the at least one indicator based at least partially on at least a portion of the data. Also, in some non-limiting embodiments, the controller may be further programmed and/or configured to activate and deactivate the at least one indicator based at least partially on at least one of the following: a transponder in communication with the at least one controller, a downward force on each support structure, or any combination thereof. In non-limiting embodiments, each support structure of the plurality of support structures may include at least two upright members, wherein each antenna is at least partially integral to at least one of the at least two upright members of a support structure.

In some non-limiting embodiments, the plurality of support structures may include at least a first support structure having a first antenna and a second support structure having a second antenna, wherein a first upright member of the first antenna includes a positive pole of the first antenna, wherein a second upright member of the first antenna includes a negative pole of the first antenna, wherein a first upright member of the second antenna includes a negative pole of the second antenna, wherein a second upright member of the second antenna includes a positive pole of the second antenna, and wherein the first upright member of the first antenna and the first upright member of the second antenna are substantially adjacent, such that fields of the first antenna and the second antenna oppose one another. Moreover, in some non-limiting embodiments, the antenna of each support structure of the plurality of support structures includes a polarity, wherein the plurality of support structures are arranged such that substantially adjacent antennae are opposing in polarity, thereby creating a null region between the substantially adjacent antennae in which fields of the substantially adjacent antennae oppose one another.

In non-limiting embodiments, the system may include a container having an interior, the interior of the container including the plurality of support structures. The container may be a cabinet in some examples. Moreover, the container may have at least one door, and the controller may be configured to read the data with the antenna for each support structure based on a state or movement of the at least one door. In non-limiting embodiments, the system may also include at least one locking arrangement configured to releasably lock an item to at least one of the plurality of support structures. In such embodiments, the controller may be further programmed and/or configured to lock and unlock the at least one locking arrangement based at least partially on user authentication. In non-limiting embodiments, the system may include at least one indicator associated with at least one support structure, wherein the controller is further configured to determine when a predetermined period of time lapses subsequent to an item being placed on the at least one support structure, and indicate that the item needs to be cleaned after the predetermined period of time lapses.

In a further preferred and non-limiting embodiment, provided is a method for tracking items supported by a plurality of support structures, including: separately interrogating each support structure of the plurality of support structures using at least one signal receiving device; receiving identification data from at least one item supported by at least one support structure of the plurality of support structures; determining, with at least one processor based at least partially on the identification data, a status or condition of the at least one item; and controlling at least one indication device associated with the at least one support structure based at least partially on the status or condition of the at least one item.

In non-limiting embodiments, determining the status or condition of the at least one item may include: searching at least one data structure for at least a portion of the identification data; and identifying the status or condition associated with the at least a portion of the identification data in the at least one data structure. In some non-limiting embodiments, controlling the at least one indication device may include: identifying a predetermined state associated with the status or condition; and changing a current state of the at least one indication device to the predetermined state.

According to another preferred and non-limiting embodiment, provided is a method for tracking items supported by a plurality of support structures, including: detecting the presence of a plurality of items being supported by the plurality of support structures by scanning each support structure of the plurality of support structures with a signal receiving device; determining, for each support structure, if the support structure is currently supporting an item based on the scan of that support structure; reading identification data from each item currently being supported by the plurality of support structures; and updating a status or condition of each item in a database.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and the claims, the singular form of "a", "an", and "the" include plural referents unless the context clearly dictates otherwise.

DESCRIPTION OF THE INVENTION

For purposes of the description hereinafter, the terms "upper", "lower", "right", "left", "vertical", "horizontal", "top", "bottom", "lateral", "longitudinal" and derivatives thereof shall relate to the invention as it is oriented in the drawing figures. However, it is to be understood that the invention may assume various alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

As used herein, the terms "communication" and "communicate" refer to the receipt, transmission, and/or transfer of one or more signals, messages, commands, or other types of data. For one unit or device to be in communication with another unit or device means that the one unit or device is able to receive data from and/or transmit data to the other unit or device. A communication may use a direct or indirect connection, and may be wired and/or wireless in nature. Additionally, two units or devices may be in communication with each other even though the data transmitted may be modified, processed, routed, etc., between the first and second unit or device. It will be appreciated that numerous other arrangements are possible.

According to a preferred and non-limiting embodiment of the present invention, an item hanger arrangement and system is used to hang, arrange, and/or support items associated with identifying data. The identifying data may be stored on the items or on separate but attachable transponders (e.g., radio frequency identification (RFID) tags or other like devices). The items may include any item suitable for hanging on a support structure, such as, but not limited to, endoscopes, tubing, pharmaceutical packages, packaging or containers holding or storing items, e.g., medical items, and/or various medical devices and equipment. The system is programmed and/or configured to receive data from the items at each individual support structure, and associate specific items (and/or type or category of item) with specific support structures. This data may be received through signal receiving arrangements that are substantially adjacent or integral with the support structures. Indicator arrangements provide a visual indication of one or more states or conditions of one or more items, such as a status, condition, attribute, and/or location of an item, based at least on the data stored thereon.

Figure 1:
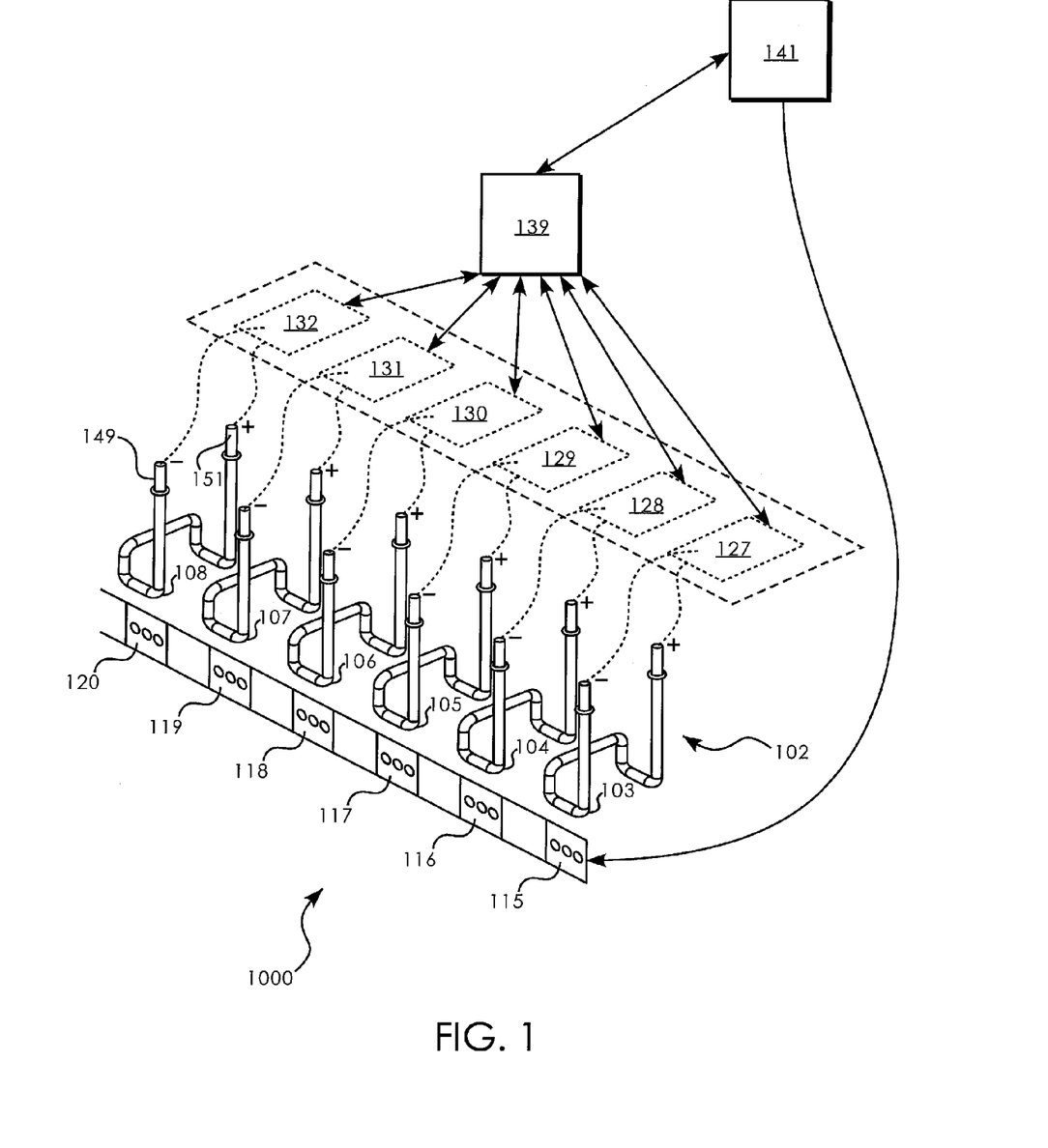
FIG. 1 is a perspective view of one embodiment of an item hanger arrangement and system according to the principles of the present invention.

Referring now to FIG. 1, an item hanger arrangement 102 and system 1000 is shown according to a preferred and non-limiting embodiment of the present invention. The item hanger arrangement 102 includes a plurality of support structures 103-108 associated with a plurality of indicator arrangements 115-120. The support structures 103-108 may hang vertically, extend horizontally, and/or extend at an angle from a surface. A plurality of signal receiving arrangements 127-132 are substantially adjacent or integral with the support structures 103-108, such that at least one signal receiving arrangement 127-132 is associated with each support structure 103-108. The signal receiving arrangements 127-132 may include one or more antennae, radio frequency identification (RFID) readers, and/or other like devices that are capable of receiving data and, in some non-limiting examples, activating a passive transponder. It will be appreciated that, in non-limiting embodiments, a single signal receiving arrangement or a number of signal receiving arrangements less than the number of support structures may be used. In such embodiments, a multiplexor or other like device may be used to enable the system 1000 to distinguish between signals being received from items on different support structures 103-108.

With continued reference to FIG. 1, the system 1000 further includes a signal receiving controller 139 in direct or indirect communication with the signal receiving arrangements 127-132 for each support structure 103-108. The signal receiving controller 139 may be adapted, programmed and/or configured to receive and process data from the signal receiving arrangements 127-132, and to route at least a portion of the data to a primary controller 141. The primary controller 141 is adapted, programmed, and/or configured to control the plurality of indicator arrangements 115-120 based at least in part on at least a portion of the data received from the signal receiving arrangements 127-132 and/or signal receiving controller 139. It will be appreciated that, in some embodiments, the primary controller 141 may include inputs to receive data directly from the signal receiving arrangements 127-132 without using a signal receiving controller 139 as an intermediary device. Further, it will be appreciated that one or more controllers may be used to perform all or some of the functions.

Still referring to FIG. 1, the primary controller 141 may include one or more computers, microprocessors, circuits, software modules, and/or other like data processing systems or devices. In a preferred and non-limiting embodiment, the controller 141 may be a specially programmed computer configured with compiled program instructions to operate and/or monitor one or more aspects of the system 1000. In other examples, the primary controller 141 may be a mobile device, remote server, microprocessor with embedded program instructions, and/or a networked computer. In some non-limiting embodiments, the signal receiving controller 139 may include a serial bus, such that the data from multiple signal receiving arrangements 127-132 may be substantially simultaneously read by the primary controller 141. For example, the signal receiving controller 139 may include a Universal Serial Bus (USB) or other like serial output. It will be appreciated that the primary controller 141 may also receive signals in parallel and/or substantially simultaneously.

In a preferred and non-limiting embodiment, and with continued reference to FIG. 1, the indicator arrangements 115-120 may include one or more light emitting members, such as light-emitting diodes (LEDs), capable of indicating at least one state. For example, each indicator arrangement may include one or more LEDs adapted and/or configured to display one or more states (e.g., conditions, statuses, attributes, or the like) by using different LEDs, different lighting patterns, different colors, and/or the like. The different states may include, for example, an alarm state, an indication that an item needs cleaning, an indication of an item location, item information and data, and/or other like statuses, conditions, and/or attributes. It will be appreciated that the indicator arrangements 115-120 may also include one or more display devices, lights, and/or audible alarms. For example, and collectively or individually, an indicator arrangement 115-120 may be a display device that displays a graphical user interface including visual representations of different states and/or other information. In a preferred and non-limiting embodiment, each indicator arrangement 115-120 is substantially adjacent a support structure 103-108. However, the indicator arrangements 115-120 may be located anywhere in the environment, such as, for example, a control panel, a door, a wall, and/or the like.

Still referring to FIG. 1, in a preferred and non-limiting embodiment, each support structure 103-108 may include a first member 149 and a second member 151. The bottom portions of the support structures 103-108, connected to the members 149, 151, may be joined, hooked, and/or shaped so as to support an item, or may simply extend horizontally or angularly to support an item. Various other support structure 103-108 configurations are possible, including horizontal or angled support members extending from a rack or wall, hooks, pegs, and/or the like. The members 149, 151 may also be part of or include the signal receiving arrangements 127-132. For example, the members 149, 150 may include a conductive material and be configured as respective positive and negative poles that form an antenna.

It will be appreciated that the item hanger arrangement 102 and system 1000 of the present invention may be implemented in numerous ways. For example, some or all components of the system 1000 may be located within a cabinet, compartment, or other storage unit. An exemplary endoscope storage cabinet is described in U.S. Pat. No. 8,414,471, titled "Endoscope storage cabinet, tracking system, and signal emitting member," which is hereby incorporated by reference in its entirety. In other examples, the item hanger arrangement 102 may include a rack that is installable on a wall or ceiling, or may be part of a free-standing floor rack. Moreover, the item hanger arrangement 102 may include support structures 103-108 that are independently connected to a wall or ceiling, without needing a common structure or panel.

In non-limiting embodiments in which a single signal receiving arrangement or a number of signal receiving arrangements less than the number of support structures are used, the specific support structures may be identified and associated with corresponding items in any number of ways. For example, the support structures may include or be attached to a transducer, sensor, accelerometer, and/or other like device capable of measuring and/or detecting a force, or lack thereof, applied to a support structure. As an example, the system 1000 may interrogate items supported by the support structures in response to an item being removed from or added to a support structure. By detecting when an item is removed from or added to a particular support structure, the system 1000 can then associate that item with that support structure and track that item as having been removed or added. It will be appreciated that numerous other arrangements may be used to distinguish between signals received from items on different support structures. For example, the signal receiving arrangement(s) may be positioned such that the support structures can be distinguished based on proximity (e.g., signal strength). Further, it will be appreciated that transducers, accelerometers, and other like sensors may also be used in embodiments in which each support structure corresponds to a signal receiving arrangement.

Figure 9:
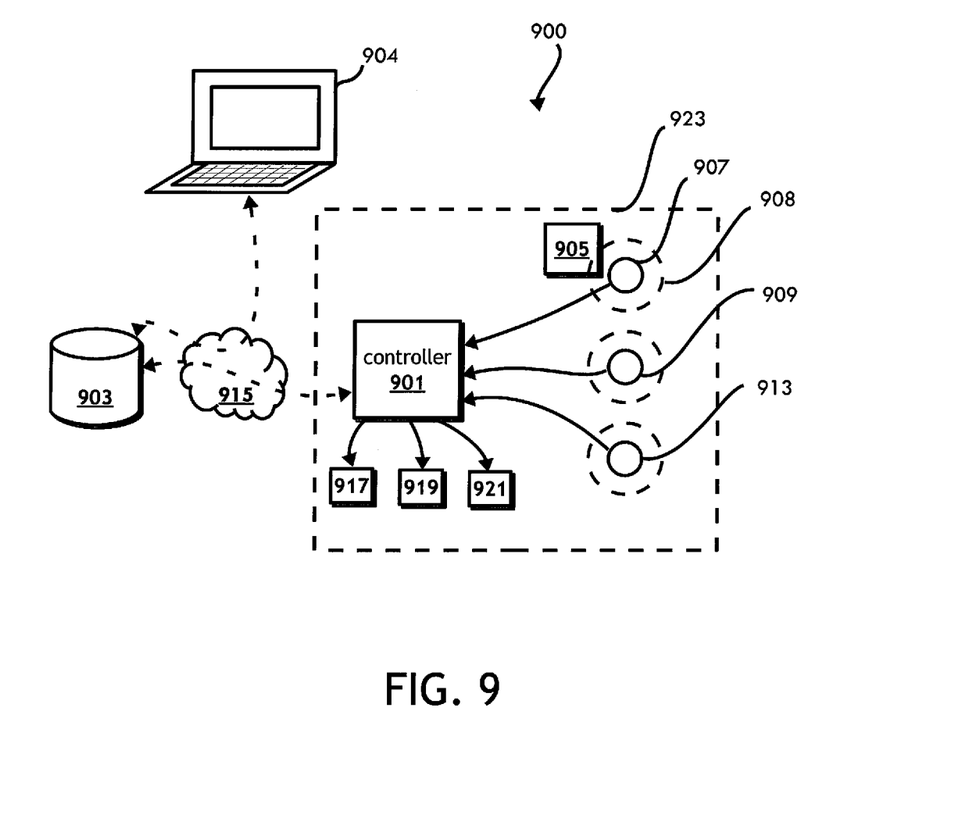
FIG. 9 is a schematic diagram of one embodiment of an item hanging and/or tracking system according to the principles of the present invention.

Referring to FIG. 9, a system 900 for storing and/or tracking items is shown according to a preferred and non-limiting embodiment. One or more controllers 901, such as but not limited to the primary controller and/or signal receiving controller described above, is in communication with indicator arrangements 917, 919, 921 and signal receiving arrangements 907, 909, 913. The indicator arrangements 917, 919, 921 may be separate arrangements or, in other embodiments, may be a display device including a graphical user interface having visual indicia representing states, such as alerts, statuses, conditions, locations, attributes, and/or the like. The signal receiving arrangements 907, 909, 913 may each be associated with a field, such as the field 908 associated with signal receiving arrangement 907, within which data can be read from one or more devices such as, but not limited to, a transponder 905. In the example shown in FIG. 9, transponder 905 may be affixed on an item (not shown) that is within the field 908 of the signal receiving arrangement 907, thereby indicating that the item is proximate to the signal receiving arrangement 907.

With continued reference to FIG. 9, the signal receiving arrangements 907, 909, 913, the indicator arrangements 917, 919, 921 and/or other components may be located on or in a container 923, such as, for example, a cabinet, drawer, closet, or the like. The controller 901 may be in communication with other devices external to the container 923, such as a database 903 and/or a central server (not shown). The controller 901 may communicate over a network environment 915, such as a local area network (LAN), the Internet, or the like. In some examples, the database 903 may include item tracking information, such as identifiers and states (e.g., locations, statuses, conditions, attributes, and/or the like). It will be appreciated by those skilled in the art that the database 903 may include one or more data structures of various types.

Still referring to FIG. 9, the transponder 905 may be affixed on an item (not shown) and placed in a cabinet 923 on a support structure (not shown) associated with a signal receiving arrangement 907. The signal receiving arrangement 907 receives data stored on the transponder 905 and communicates it to the controller 901. The controller 901 may then store at least a portion of the data in the database 903 and/or control the indicator arrangements 917, 919, 921 based on the data or other information. For example, the data on the transponder 905 may identify an item (or type or category of item). The controller 901 may then search the database 903 for that item (or type or category of item), based on an identifier, to determine any further information concerning the item (or type or category of item). The controller 901 may also store information in the database 903, such as the current location of the item, a status or condition that was stored on the transponder 905, and/or the like.

With continued reference to FIG. 9, a user computer 904 may be in communication with the database 903 and/or controller 901 via the network environment 915. The user computer 904 may therefore view and/or modify information concerning the items that are stored in the container 923 and/or other containers via one or more graphical user interfaces provided by client software, web applications, and/or the like. One or more servers, such as but not limited to an HTTP server, may also be in communication with the database 903 and provide content to user computers 904 based at least partially on data retrieved from the database 903.

Figure 2:
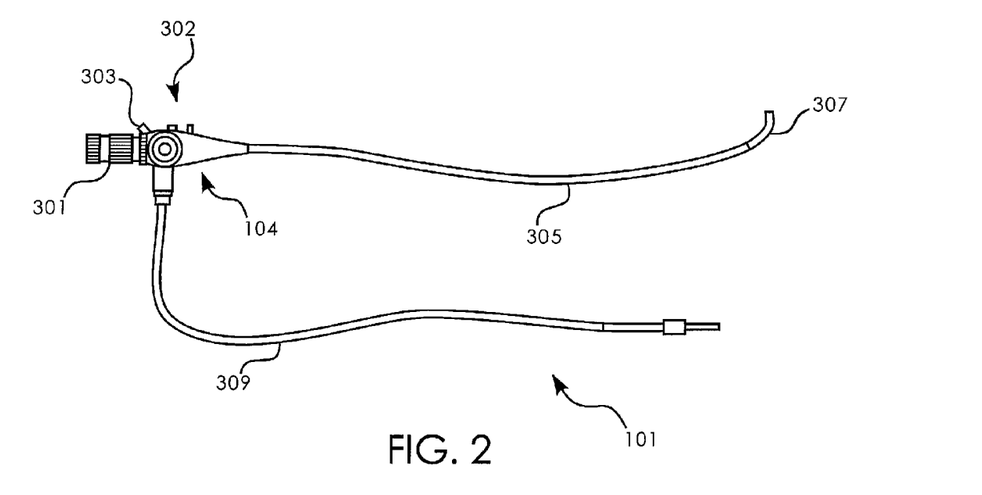
FIG. 2 is a side view of an endoscope according to the principles of the present invention.

Referring to FIG. 2, an endoscope 101 is shown having a first end 302 including an eyepiece 301 and an opening 303 for wires and instruments. From the first end 302, a flexible shaft 305 extends to a second end that includes a flexible tip 307. Another flexible shaft 309 extends from the first end 302 for transmitting light, air, and/or fluids. A transponder 104 or other like signal emitting member is located on the first end 302 of the endoscope 101 to enable accurate reading by the signal receiving arrangements 127-132 of the system 1000. Although FIGS. 2 and 3 depict endoscopes as exemplary items to be used with the item hanger arrangement 102 and system 1000, it will be appreciated that numerous other items may be used.

Figure 3:
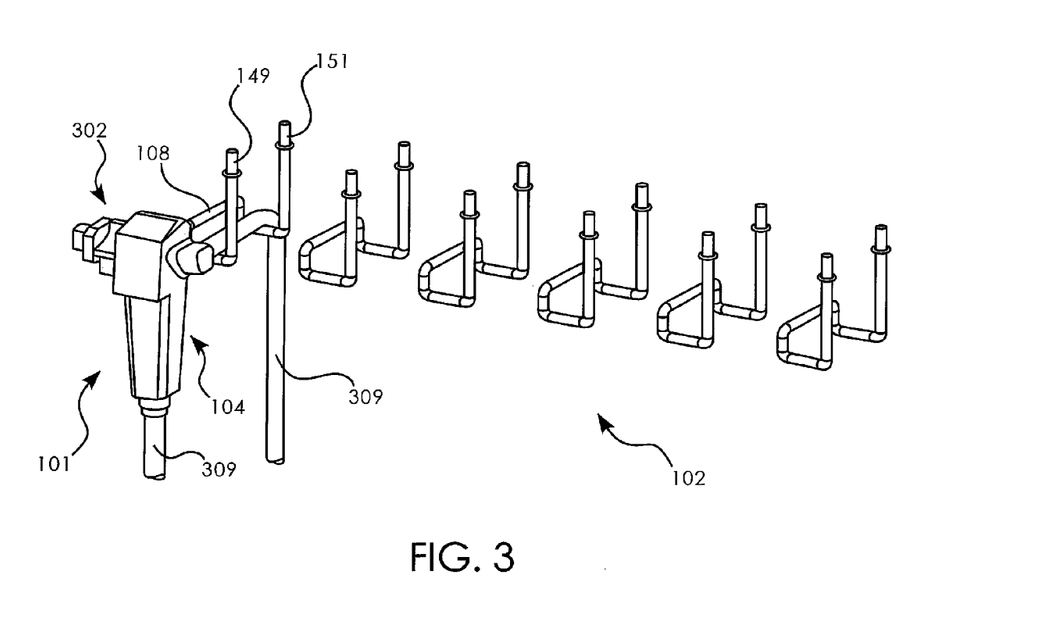
FIG. 3 is a perspective view of an item hanger arrangement supporting an endoscope according to the principles of the present invention.

Referring now to FIG. 3, a preferred and non-limiting embodiment of an item hanger arrangement 102 is shown. In this example, the item 101 is an endoscope as shown in FIG. 2. The endoscope 101 has a transponder 104 and rests upon a horizontal portion of the support structure 108 that extends from the upright members 149, 151. The first end 302 of the endoscope 101 is substantially adjacent the support structure 108 and is at least partially supported by the flexible shaft 309 of the endoscope 101. The flexible shaft 309 rests on a portion of the support structure 108, allowing both shafts 305, 309 of the endoscope 101 to hang from either side of the support structure 108. However, it will be appreciated that various other arrangements and configurations may be used to hang the endoscope 101, or other item, from the support structure 103.

Figure 6:
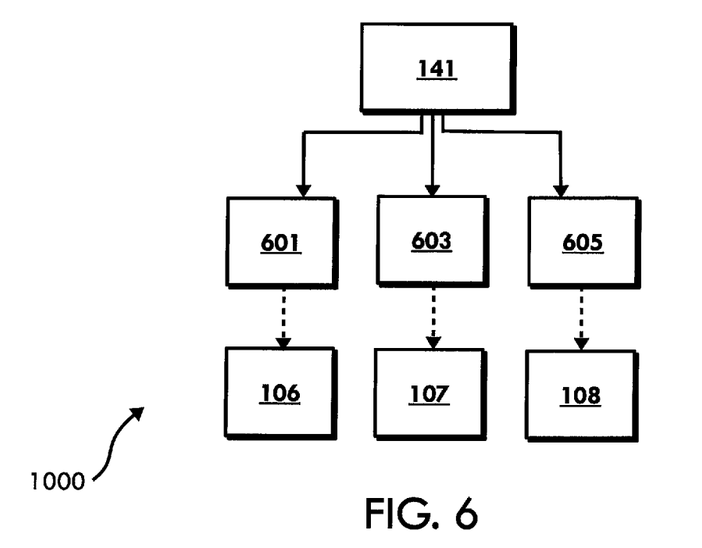
FIG. 6 is a schematic diagram of one embodiment of an item hanger arrangement and system according to the principles of the present invention.

In a preferred and non-limiting embodiment, one or more locking arrangements may be provided to secure an item 101 to a support structure 103-108. For example, referring to FIG. 6, a non-limiting embodiment is shown in which locking arrangements 601, 603, 605 are in communication with a controller 141 and are at least partially integral with or substantially adjacent support structures 106, 107, 108. A locking arrangement 601, 603, 605 may include a locking mechanism that fits over or around the item 101 while on the support structure 106-108. The locking mechanism may be configured to be locked and unlocked manually, through the use of a key, or electronically through received signals and/or commands.

In some non-limiting embodiments, the system 1000 is adapted, programmed, and/or configured to authenticate a user based on the user's credentials and a database of authorized personnel. The user's credentials may include data stored on a personalized transponder, a password or digital signature, a fingerprint scan or other biometric input, and/or the like, or may be entered by a user through an input device (e.g., keyboard, mouse, touch screen, etc.). Moreover, a user's credentials may also be used to associate a particular user with an item 101 when it is removed and/or returned to the item hanging arrangement 102, thereby tracking users' interactions with an item 101 over time. It will be appreciated that various other arrangements and configurations are possible.

In a preferred and non-limiting embodiment and with continued reference to FIG. 1, the controller 141 may be adapted, programmed, and/or configured to control the indicator arrangements 115-120 based at least partially on data received from the signal receiving arrangements 127-132. For example, after the items 101 on the hanger arrangement 102 have been interrogated and read by the signal receiving arrangements 127-132, the controller 141 may access one or more databases or other like data structures to determine a state of the item, such as one or more statuses, conditions, locations, attributes, alerts, and/or the like. Each item 101 may be associated with a unique identifier that corresponds in the database to additional information. It will be further appreciated that the state information may also be stored on the transponder 104 associated with the item 101, and does not need to be stored in a separate database. Moreover, states may also be displayed on various other devices in communication with the system 1000, such as personal computers and/or mobile devices.

In non-limiting embodiments, a status may indicate that the item 101 is in an unclean condition or state. For example, the database may indicate that an item needs to be cleaned after the item is used for a procedure or is removed from a storage location. When the item is returned to the item hanger arrangement 102 without being cleaned (i.e., without the status being changed in the database), the indicator arrangement corresponding to the support structure on which the item is placed may display, emit, and/or transmit an alert. For example, the indicator arrangement 120 for the support structure 108 supporting the item 101 may display a red, blinking light (or, for example, transmit an alarm message, an alarm sound, an alarm email, an alarm text, and/or the like). Items may also be designated as unclean after being stored for a predetermined period of time. For example, endoscopes can generally be stored for seven (7) to fourteen (14) days before accumulating a sufficient amount of dust, particles, and other elements to render it unclean or unfit for use. After this period of time, the system 1000 may automatically indicate that the endoscope needs to be cleaned through an alert on an associated indicator arrangement. Other statuses may include an alarm condition, a location, a repair or maintenance alert, and/or the like. Alerts may also be transmitted to a remote device or system, such as a computer, mobile phone, central management system, and/or the like. The alerts may be communicated via text messaging (e.g., SMS), email, voicemail, push-messaging, and/or other like communication methods or protocols.

In a preferred and non-limiting embodiment, each signal receiving arrangement 127-132 may be associated with a unique identifier and be in a fixed location relative to other signal receiving arrangements 127-132. With such a configuration, the unique identifier of a particular signal receiving arrangement 127-132 may be associated with the unique identifier of an item 101, allowing for the system 1000 to particularly identify and track the location of each item 101 with respect to each support structure 103-108. In non-limiting embodiments, the identification of the signal receiving arrangements 127-132 may depend upon how the signal receiving arrangements 127-132 are connected to the signal receiving controller 139 (e.g., based on port assignments).

Figure 4A:
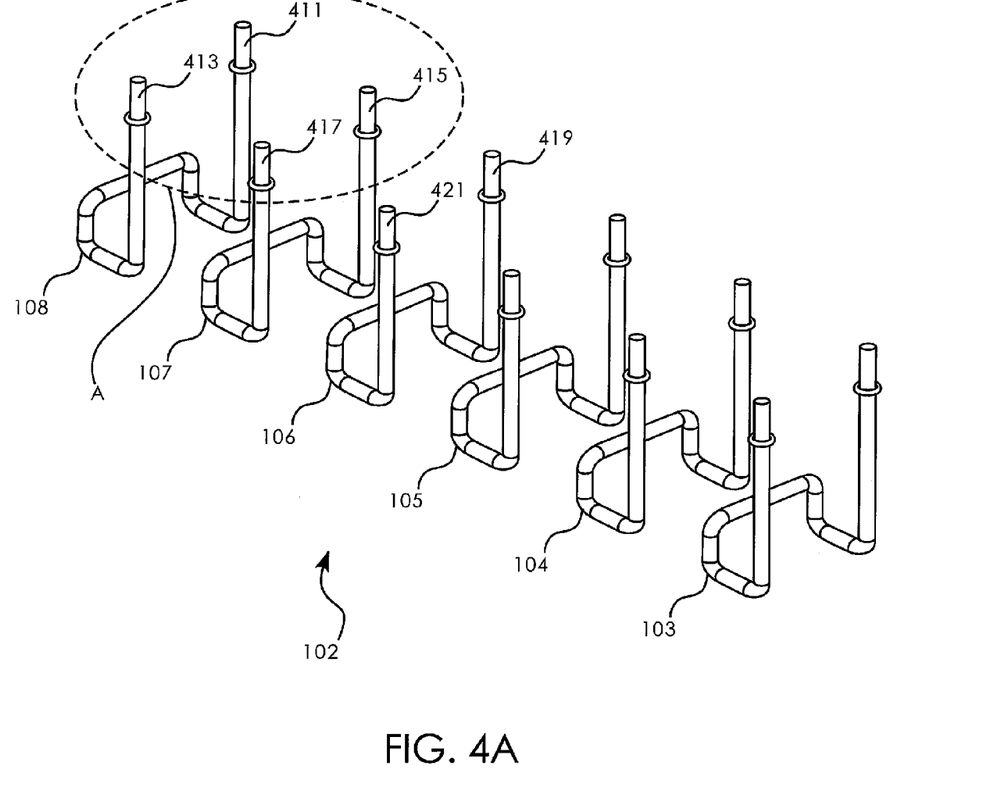
FIG. 4A is a perspective view of the item hanger arrangement of FIG. 3.

Referring now to FIG. 4A, an item hanger arrangement 102 is shown according to a preferred and non-limiting embodiment. The hanger arrangement 102 includes a plurality of support structures 103-108, each support structure having two upright members 411, 413, 415, 417, 419, 421. The upright members may include a conductive material and be part of a signal receiving arrangement for the associated support structure. For example, upright members 411, 413 for a support structure 108 may include a conductive material and act as an antenna that is at least partially integral with the members 411, 413. Upright member 413 may include a positive pole of the antenna, and upright member 411 may include a negative pole of the antenna. It will be appreciated that the support structures 103-108 may each include the same material or, in other embodiments, portions of the support structures 103-108 may include different material from the upright members 411, 413, 415, 417, 419, 421. For example, the upright members 411, 413 of support structure 108 may include one or more conductive materials that are not present in all of the support structure 108 (e.g., not present in the bottom portion of the support structure 108 that connects the upright members 411, 413). It will be appreciated that numerous other arrangements are possible, and that various types of materials may be used.

In a preferred and non-limiting embodiment, and with continued reference to FIG. 4A, a support structure 107 may reverse the polarities of the upright members 415, 417 from those of an substantially adjacent support structure 108 such that upright member 417 includes a negative pole of an antenna, and upright member 415 includes a positive pole of an antenna. In this manner, substantially adjacent upright members 413, 417 and 411, 413 of two different but substantially adjacent support structures 108, 107 are of opposite polarities. The next substantially adjacent support structure 106 may also be reversed from substantially adjacent support structure 107, such that upright member 421 is a positive pole and upright member 419 is a negative pole. This reverse polarity configuration aids in preventing interference between the fields emitted by the signal receiving arrangements associated with substantially adjacent support structures 108, 107, 106.

Figure 4B:
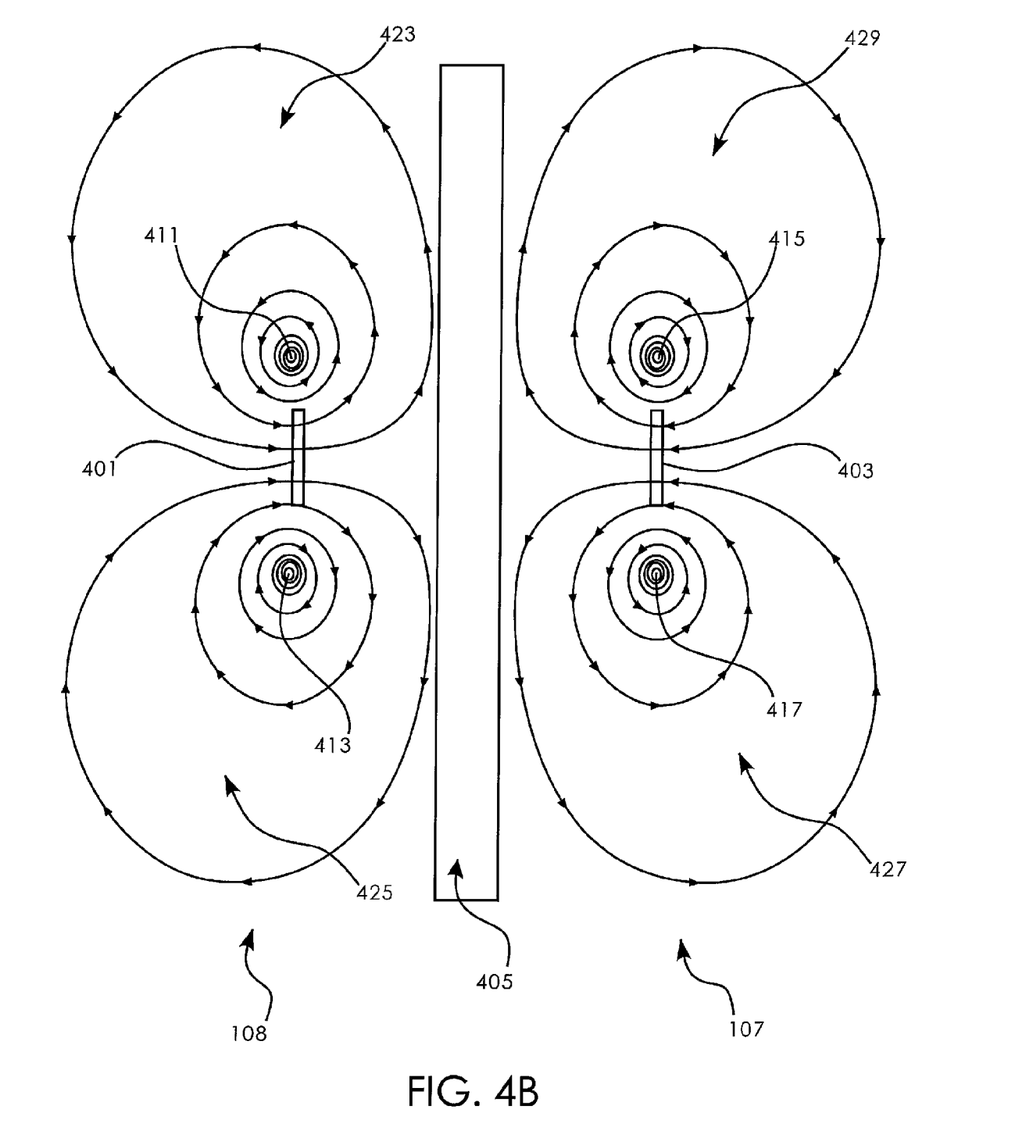
FIG. 4B is a top view of two support structures shown in the area A of the item hanger arrangement of FIG. 4A.

Referring now to FIG. 4B, a top view perspective of area A shown in FIG. 4A is illustrated according to a preferred and non-limiting embodiment, including upright members 411, 413, 415, 417. In this example, the upright members 411, 413, 415, 417 have alternating polarities to produce a null region 405 between the support structures 108, 107. Through the use of a configuration that reverses the polarity of substantially adjacent antennae, the fields 423, 425 produced from the upright members 411, 413 of a first support structure 108 oppose the fields 427, 429 produced from the upright members 415, 417 of a second support structure 107. The system can therefore communicate with transponders 401, 403 in isolation without concern for overlapping fields, because the substantially adjacent fields oppose one another. The null region 405 produced by this reverse polarity configuration may avoid the need to use shielding elements between substantially adjacent support structures 108, 107 and/or signal receiving arrangements. However, it will be appreciated that, in some non-limiting embodiments, shielding elements may be used in combination with, or in place of, a reverse polarity configuration of signal receiving arrangements.

Figure 4C:
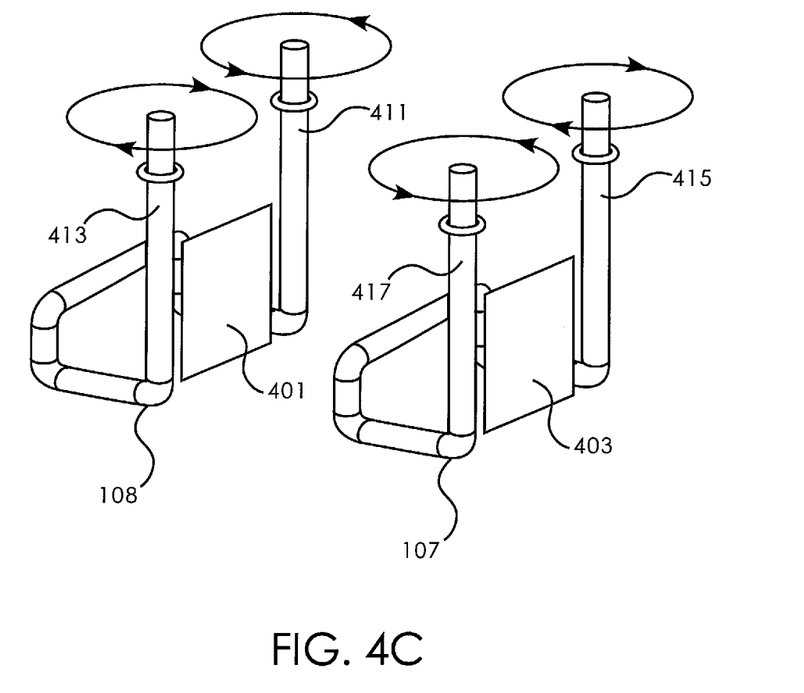
FIG. 4C is a perspective view of the two support structures shown in the area A of the item hanger arrangement of FIG. 4A.

Referring now to FIG. 4C, a perspective view of the support structures in area A shown in FIG. 4A is illustrated, including transponders 401, 403, according to a preferred and non-limiting embodiment. FIG. 4C depicts a first support structure 108 having a first upright member 411 and a second upright member 413. A transponder 401 is located between the upright members 411, 413. Each upright member 411, 413 of the first support structure 108 is of opposite polarities. Likewise, the support structure 107 includes a first upright member 415 and a second upright member 417. The first upright member 415 of support structure 107 has a polarity that is the opposite of a polarity of second upright member 417 of support structure 107. A transponder 403 is located between the upright members 415, 417, as it may be when items are supported by the members 415, 417.

Figure 4D:
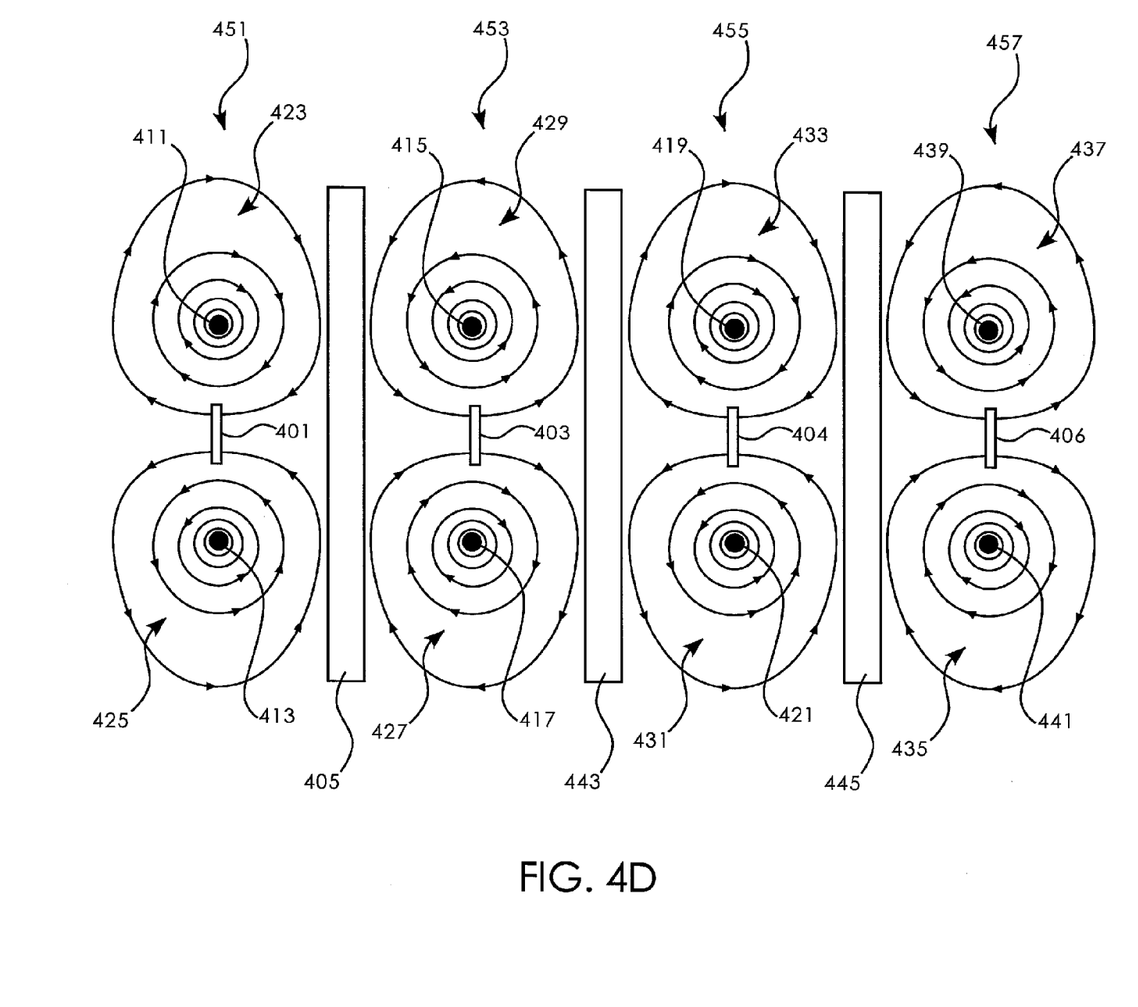
FIG. 4D is a top view of an item hanger arrangement according to the principles of the present invention.

Referring now to FIG. 4D, a top view perspective view of an item hanging arrangement is shown according to a preferred and non-limiting embodiment. In this example, four signal receiving arrangements are shown. A first signal receiving arrangement 451 includes upright members 411, 413, which are respectively associated with fields 423, 425 having opposing polarities. For example, field 423 may be positive and field 425 may be negative. A second signal receiving arrangement 453 includes upright members 415, 417, which are respectively associated with fields 427, 429 having opposing polarities. For example, field 427 may be positive and field 429 may be negative. Thus, field 427 opposes both field 429 and field 425, and field 429 opposes both field 427 and 423. A third signal receiving arrangement 455 includes upright members 419, 421, which are respectively associated with fields 431, 433 having opposing polarities. For example, field 433 may be positive and field 431 may be negative. A fourth signal receiving arrangement 457 includes upright members 439, 441, which are respectively associated with fields 435, 437 having opposing polarities. For example, field 435 may be positive and field 439 may be negative. As arranged in this example, null regions 405, 443, 445 are created from the opposing fields.

Figure 8A:
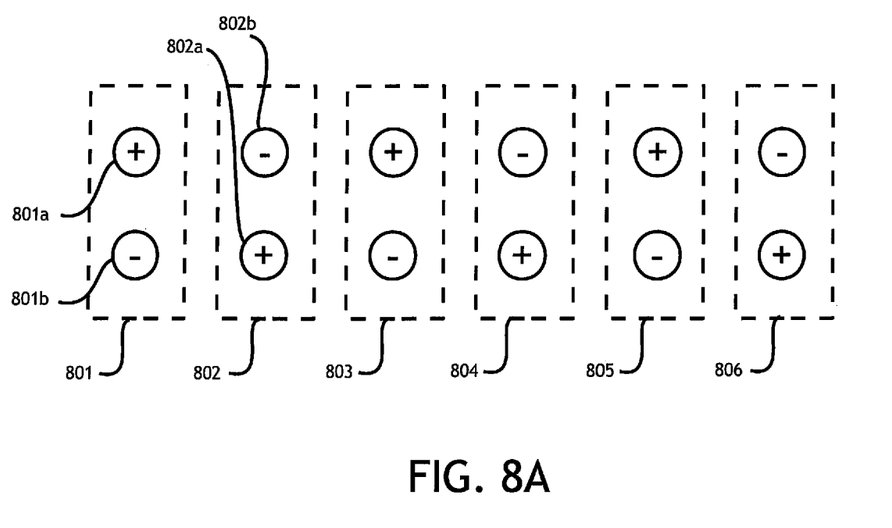
FIG. 8A is a top view of an item hanger arrangement according to the principles of the present invention.
Figure 8B:
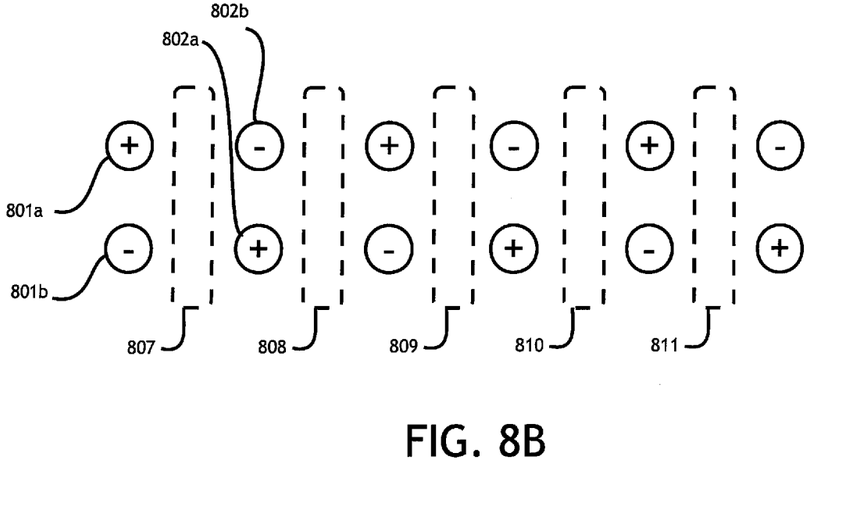
FIG. 8B is another top view of the item hanger arrangement shown in FIG. 8A.

Referring now to FIGS. 8A and 8B, another top view perspective is shown of an item hanging arrangement according to a non-limiting embodiment. Referring first to FIG. 8A, a plurality of support structures 801-806 are shown. Each support structure 801-806 includes a positive pole and a negative pole of a signal receiving arrangement, such as an antenna. For example, support structure 801 includes positive pole 801a and negative pole 801b, and support structure 802 includes positive pole 802a and negative pole 802b. As shown in the embodiment depicted in FIG. 8A, the arrangement of poles for each support structure 801-806 alternates such that, for example, the positive pole 801a of a first support structure 801 is substantially adjacent a negative pole 802b of a second support structure 802. Likewise, the negative pole 801b of the first support structure 801 is substantially adjacent a positive pole 802a of the second support structure 802. As explained herein, in some non-limiting embodiments the poles 801a, 801b may be part of, or at least partially integrated into, respective members of a support structure 801. However, it will be appreciated that numerous other arrangements are possible with different types of support structures.

Referring now to FIG. 8B, the item hanging arrangement of FIG. 8A is shown according to a preferred and non-limiting embodiment. FIG. 8B depicts a plurality of null regions 807-811 that are created by the reverse polarity configuration of the signal receiving arrangements for the support structures 801-806 shown in FIG. 8A. The null regions 807-811 represent a space that excludes the respective fields of the signal receiving arrangements, or in which the respective fields are weak, due to the opposition of substantially adjacent fields resulting from the alternating plurality arrangement of the poles 801a, 801b, 802a, 802b. It will be appreciated that the null regions 807-811 may take on various forms due to the magnitude and position of the respective fields of the signal receiving arrangements and environmental conditions.

Figure 5:
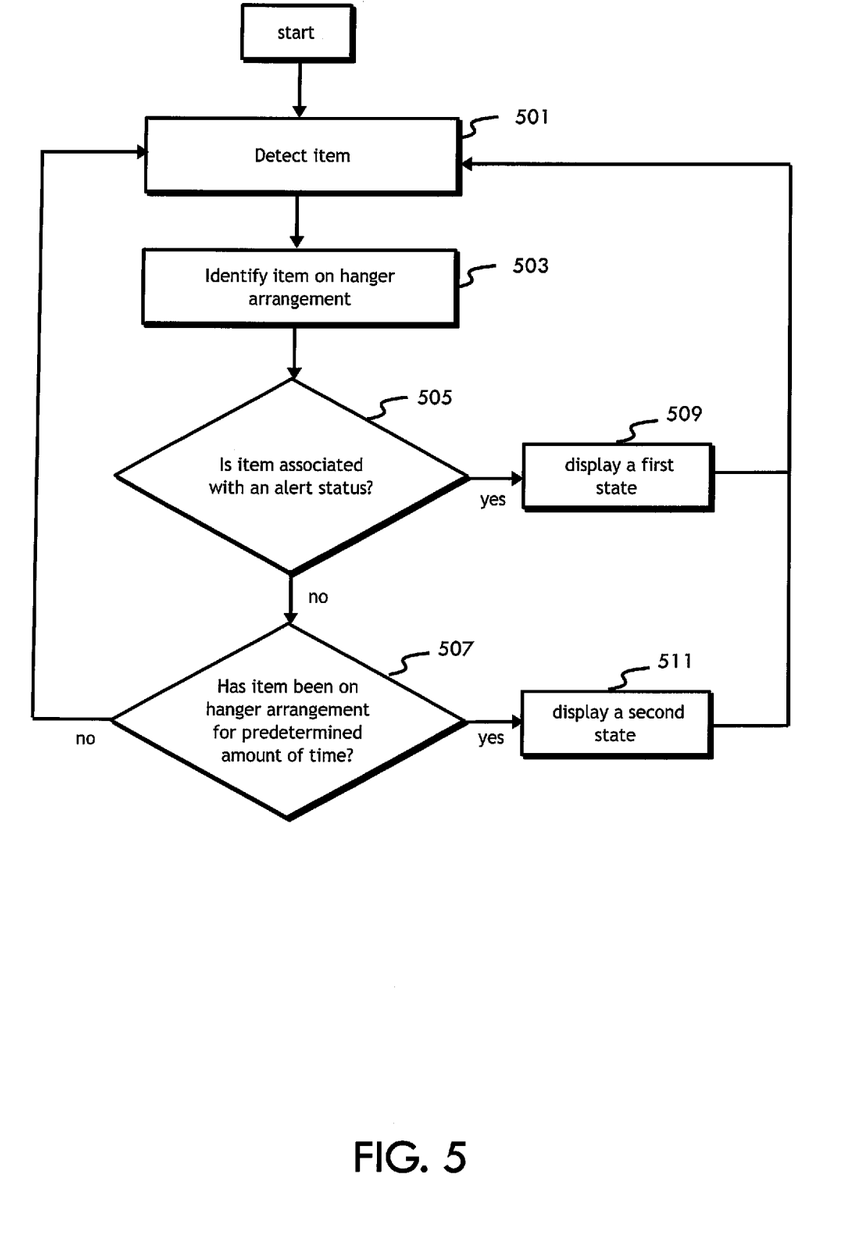
FIG. 5 is a step diagram for one embodiment of an item hanger arrangement, system, and method according to the principles of the present invention.

Referring now to FIG. 5, a method for tracking items on an item hanging arrangement is shown according to a preferred and non-limiting embodiment of the present invention. At a first step 501, an item is detected on a support structure through either an interrogation of a transponder on the item, or through a force experienced by the support structure when the item is placed thereon. Once the item is detected, at a next step 503, the item on the support structure of the hanger arrangement is identified by receiving a unique identifier from the item or from a transponder located on the item. Once the unique identifier is determined, at a next step 505 a database is queried to determine if the item has a state that indicates a condition or status requiring an alert. If there is an alert status associated with the item, the method proceeds to step 509, in which a first state is displayed by an associated indicator arrangement, and then to step 501 to wait for the next detection. If an alert status is not associated with the item, the method proceeds to step 507 in which a determination is made whether the item has been on the hanger arrangement for a predetermined amount of time. If the predetermined amount of time has been met or exceeded, the method proceeds to step 511 in which a second state is displayed by an associated indicator arrangement, and then to step 501 to wait for the next detection.

Figure 7:
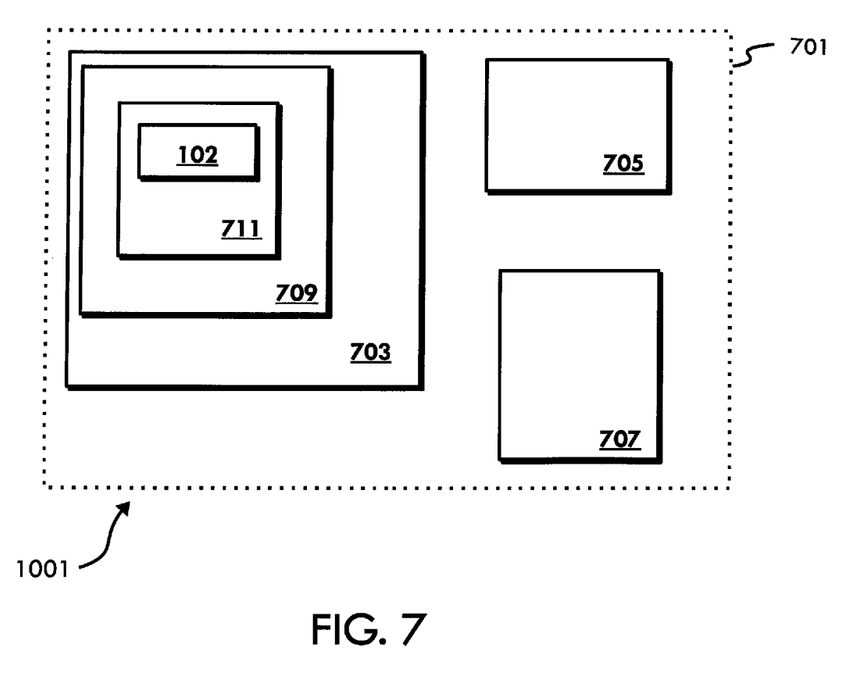
FIG. 7 is a schematic diagram of one embodiment of an item tracking system according to the principles of the present invention.

Referring now to FIG. 7, an item tracking system 1001 is shown according to a further preferred and non-limiting embodiment of the present invention. The example depicted in FIG. 7 illustrates how an item (not shown) on an item hanger arrangement 102 may be tracked throughout a facility 701, such as but not limited to a hospital campus. The facility 701 may include one or more buildings 703, 705, 707 in a single area or, in some examples, may include multiple remote locations each including one or more buildings, rooms, departments, and/or the like. In the example shown in FIG. 7, the facility 701 includes a building 703 having a department 709. Multiple departments may exist in one building 703 or across multiple buildings. The department 709 includes a secured room 711 having an item hanger arrangement 102 therein. The department 709 may include one or more secured rooms, storage areas, and/or the like. The item tracking system 1001 therefore allows for items to be tracked throughout the facility 701 based on location.

Still referring to FIG. 7, as an example of the item tracking system 1001, a user may remove an item from a particular support structure of an item hanger arrangement 102 in a secured room 711 of a department 709 in a building 703. To remove the item, the user may input credentials such as, for example, scanning an identifying transponder, inputting a login and/or password, inputting a fingerprint or other biometric, and/or the like. The user is associated with the removed item, which is associated with the particular support structure and item hanger arrangement 102 that previously supported the item. If the user removes the item to another department or to another building 705, 707 in the facility 701, the item may be tracked to this new location. In this manner, a manager or administrator may locate the removed item. Further, an indicator arrangement (not shown) of the item hanger arrangement 102 may indicate the current location and/or status of the item. It will be appreciated that various other arrangements are possible.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system for supporting and tracking at least one item, comprising: a plurality of support structures, each support structure adapted to support at least one item; at least one signal receiving arrangement associated with the plurality of support structures, wherein the at least one signal receiving arrangement is configured to receive data from a transponder associated with the at least one item; at least one indicator arrangement associated with the plurality of support structures; and at least one controller in communication with the at least one signal receiving arrangement and the at least one indicator arrangement, the at least one controller programmed and/or configured to control the plurality of indicator arrangements based at least partially on at least a portion of the data received from the at least one signal receiving arrangement;

wherein each support structure comprises at least two upright members, and wherein at least a portion of at least one upright member of each support structure comprises at least a portion of the at least one signal receiving arrangement;

wherein at least a portion of the at least two upright members comprises at least a portion of the at least one signal receiving arrangement;

the at least one signal receiving arrangement comprises at least a first antenna and a second antenna, wherein a first upright member of the first antenna comprises a positive portion of the first antenna, wherein a second upright member of the first antenna comprises a negative portion of the first antenna, wherein a first upright member of the second antenna comprises a negative portion of the second antenna, wherein a second upright member of the second antenna comprises a positive portion of the second antenna, and wherein the first antenna and second antenna are arranged such that the first upright member of the first antenna and the first upright member of the second antenna are substantially adjacent.

2. The system of claim 1, further comprising a plurality of transponders, wherein each transponder of the plurality of transponders is adapted to be fixed on or associated with an item.

3. The system of claim 2, wherein each transponder comprises at least a portion of the data received by the at least one signal receiving arrangement, and wherein the data comprises an identifier that uniquely identifies the at least one item in at least one data structure.

4. The system of claim 1, wherein the at least one indicator arrangement comprises a plurality of indicator arrangements, wherein each indicator arrangement of the plurality of indicator arrangements corresponds to a support structure of the plurality of support structures, and wherein the at least one controller is further programmed and/or configured to cause each indicator arrangement to indicate at least one state of at least one item supported by the corresponding support structure.

5. The system of claim 4, wherein the at least one state indicates at least one of the following: an alarm, a condition, a location, or any combination thereof.

6. The system of claim 4, wherein each indicator arrangement is substantially adjacent its corresponding support structure.

7. The system of claim 1, wherein the at least one controller is further programmed and/or configured to cause the at least one indicator arrangement to indicate at least one state of at least one item supported by the corresponding support structure, wherein the at least one item is a medical device, and wherein the at least one state comprises at least one of the following: an indication that the medical device is clean, an indication that the medical device requires cleaning, an indication that the medical device has been removed from the support structure, an indication that the medical device has been removed from a facility or location, an indication that the medical device needs requires repair, or any combination thereof.

8. The system of claim 1, further comprising at least one locking device configured to releasably lock an item to at least one of the plurality of support structures, wherein the at least one controller is programmed and/or configured to operate the at least one locking device based at least partially on user authentication.

9. The system of claim 1, wherein the at least one indicator arrangement comprises at least one display device that displays a graphical user interface, the graphical user interface comprising at least one visual indication of at least one state of at least one item.

10. The system of claim 1, further comprising a container having an interior, the interior of the container comprising the plurality of support structures, wherein the container has at least one door, and wherein the controller is configured to read the data with the signal receiving arrangement for each support structure based on a state or movement of the at least one door.

* * * * *